US006906218B2

(12) United States Patent
Allgeier et al.

(10) Patent No.: US 6,906,218 B2
(45) Date of Patent: Jun. 14, 2005

(54) CYCLOHEXANE DERIVATIVES AND METHODS FOR THEIR PREPARATION

(75) Inventors: Alan M. Allgeier, Wilmington, DE (US); Christian P. Lenges, Wilmington, DE (US)

(73) Assignee: Invista North America S.a.r.l., Wilmington, DE (US)

(*) Notice: Subject to any disclaimer, the term of this patent is extended or adjusted under 35 U.S.C. 154(b) by 0 days.

(21) Appl. No.: 10/322,273

(22) Filed: Dec. 18, 2002

(65) Prior Publication Data

US 2004/0122252 A1 Jun. 24, 2004

(51) Int. Cl.$^7$ ............................................. C07C 255/03
(52) U.S. Cl. ...................................................... 558/430
(58) Field of Search ........................................ 558/430

(56) References Cited

U.S. PATENT DOCUMENTS

| | | | |
|---|---|---|---|
| 3,686,303 A | * | 8/1972 | Knowles .................. 260/465.5 |
| 4,760,052 A | * | 7/1988 | Callahan et al. .............. 514/11 |
| 5,153,354 A | | 10/1992 | Schroder et al. |
| 5,512,695 A | | 4/1996 | Kreutzer et al. |
| 5,512,696 A | | 4/1996 | Kreutzer et al. |
| 5,523,453 A | | 6/1996 | Breikss |
| 5,663,369 A | | 9/1997 | Kreutzer et al. |
| 5,688,986 A | | 11/1997 | Tam et al. |
| 5,693,843 A | | 12/1997 | Breikss et al. |
| 5,723,641 A | | 3/1998 | Tam et al. |
| 5,847,191 A | | 12/1998 | Bunel et al. |
| 5,959,135 A | | 9/1999 | Garner et al. |
| 6,120,700 A | | 9/2000 | Foo et al. |
| 6,171,996 B1 | | 1/2001 | Garner et al. |
| 6,171,997 B1 | | 1/2001 | Foo et al. |
| 6,399,534 B2 | | 6/2002 | Bunel et al. |

FOREIGN PATENT DOCUMENTS

EP   0 495 175   3/1995

OTHER PUBLICATIONS

DN 124:260012, DN DN 114:62379.*
DN 122:187242, DN89:163108.*
DN 121:280954.*
DN 121:133236.*
Suh et al.,*Facile Syntheses of cis–Fused Carbobicycles via Combination of Ciafsen Rearrangement of Macrolactone and Nitrile Oxide Cycloaddition*, Chemistry Letters, pp. 63–66, 1994.
Int'l Search Report for PCT/US03/40247, May 27, 2004.
Rienaecker, Brennstoff. Chemie, vol. 45, p. 206 (1964).

* cited by examiner

*Primary Examiner*—James O. Wilson
*Assistant Examiner*—Ebenezer Sackey

(57) ABSTRACT

Disclosed herein are methods for preparing nitrile derivatives and their corresponding amines from 1-,2-,4-trivinylcyclohexane by hydrocyanation, followed by hydrogenation. Also disclosed are novel compounds used in the methods described herein.

14 Claims, No Drawings

CYCLOHEXANE DERIVATIVES AND METHODS FOR THEIR PREPARATION

FIELD OF THE INVENTION

The present invention discloses novel organonitrile and organoamine compounds and methods for making them comprising hydrocyanation and hydrogenation reactions, respectively. Specifically, disclosed are cyclohexane derivatives containing nitrile groups and cyclohexane derivatives containing amine groups.

BACKGROUND OF THE INVENTION

Cyclohexane derivatives containing nitrile groups are of great interest as precursors to a variety of useful molecules with applications as monomers for the production of polymers, or as fragrance intermediates.

1,2,4-trivinylcyclohexane, which is used as a starting material in the method according to the present invention, can be obtained, for example, according to Rienaecker, Brennstoff-Chemie, Vol. 45, p. 206 (1964), by pyrolysis of 1,5,9-cyclododecatriene.

Prior to the present invention, it was not known that trivinylcyclohexane could be converted to cyclohexane derivatives with nitrile groups by employing a hydrocyanation process. It was also not known that the so formed cyclohexane derivatives containing nitrile groups could be converted selectively in a hydrogenation process to the cyclohexane derivatives with the corresponding amine groups. There is a need to access cycloaliphatic hydrocarbons, which have one or more functional groups, such as nitriles, amines, alcohols or carboxylic acids. Especially cycloaliphatic hydrocarbons with two and more than two functional groups are of interest.

Thus, there is a need for cyclohexane derivatives, which contain nitrile groups. There also remains a need for a method to produce cyclohexane derivatives, which contain nitrile groups. There is a need for cyclohexane derivatives, which contain amine groups. There remains also a need for a method to produce cyclohexane derivatives, which contain amine groups. These needs are met by the present invention.

SUMMARY OF THE INVENTION

The present invention provides for a composition of matter for cyclohexane derivatives, said composition comprising a cyclohexane derivative of the formula (I-A) having nitrile groups:

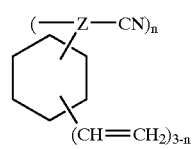
(I-A)

wherein (I-A) is alone or in combination with isomers thereof, and wherein substituents on the cyclohexane ring are in the 1-, 2-, and 4-positions, and wherein Z is a —CH$_2$CH$_2$— group or a:

group, and n is an integer of 1 to 3.

The present invention provides also for a method for preparing a compound of the formula (I-A):

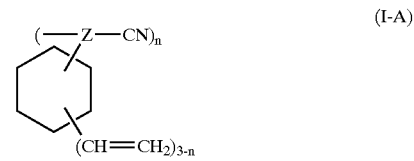
(I-A)

either alone or in combination with isomers thereof, and wherein substituents on the cyclohexane ring are in the 1-, 2- and 4-positions, and wherein Z is a —CH$_2$CH$_2$— group or a:

group, and n is an integer of 1 to 3; said method comprising contacting 1,2,4-trivinylcyclohexane with hydrogen cyanide, in the presence of a catalyst, said catalyst comprising an organic phosphorous ligand and a Group VIII metal, wherein said contacting is done at a temperature of from about −25° C. to about 200° C.

Also disclosed is a composition of matter comprising a cyclohexane derivative of the formula (I-B):

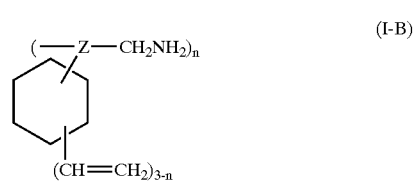
(I-B)

either alone or in combination with isomers thereof, wherein the substituents on the cyclohexane ring are in the 1-, 2- and 4-positions, Z is a —CH$_2$CH$_2$— group or a:

group, and n is an integer of 1 to 3.

Another disclosure is composition of matter having the formula XVIII, XIII, XXI or XXVI:

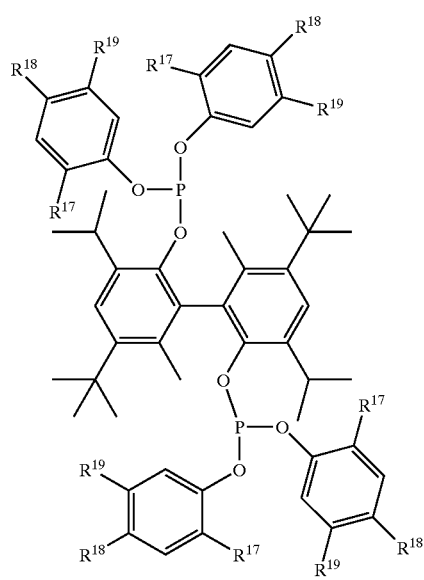
XVIII
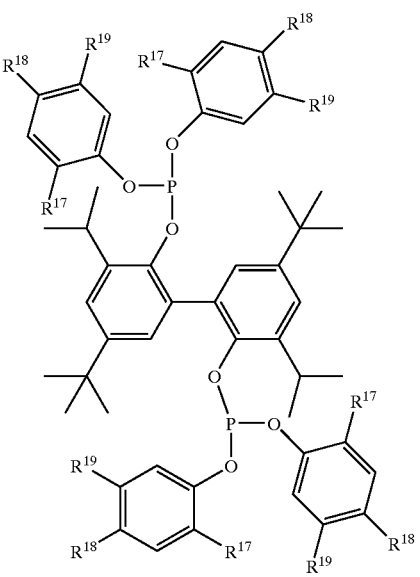
XXI
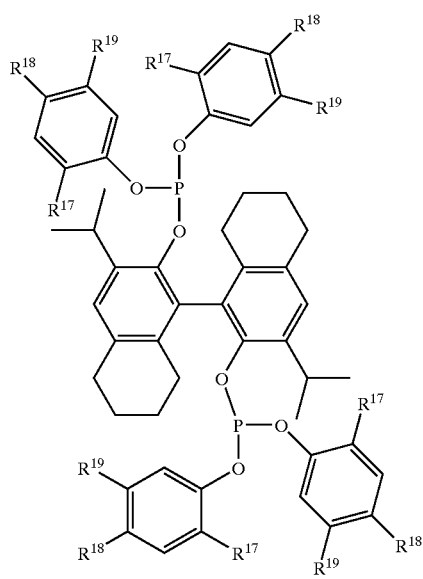
XIII
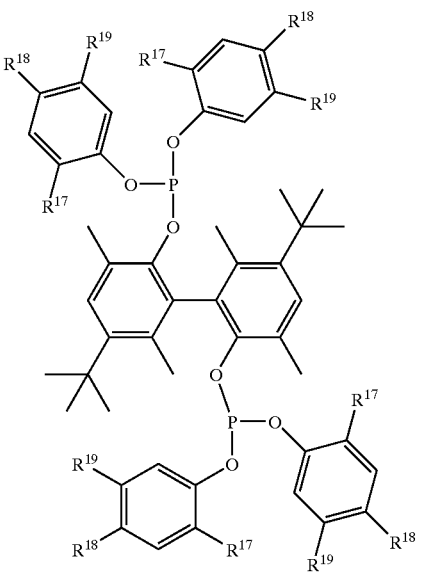
XXVI wherein $R^{17}$ is selected from the group consisting of H, methyl, ethyl and isopropyl, and wherein $R^{18}$ and $R^{19}$ are independently H or methyl.

DETAILED DESCRIPTION OF THE INVENTION

It is one object of the present invention to provide novel cyclohexane derivatives having nitrile groups, achieved by hydrocyanation followed by hydrogenation to their corresponding amines. It is another object of the present invention to provide a method for preparing such cyclohexane derivatives. These and other objects will become apparent in the following detailed description.

Cyclohexane derivatives containing nitrile groups of formula (I-A):

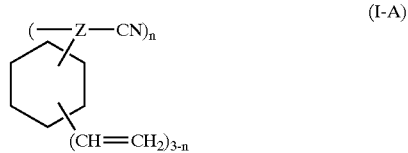

(I-A)

either alone, as combinations of these, and/or isomers of these, in which the substituents on the cyclohexane ring are in the 1-, 2-, and 4-positions, Z is a —$CH_2CH_2$— group or a:

group, and n is an integer of 1 to 3, are obtained by the hydrocyanation of 1,2,4-trivinylcyclohexane. These compounds are useful as precursors for monomers for the formation of polymers and as precursors for other useful molecules. For instance, they can be converted to corresponding amines of the formula (I-B):

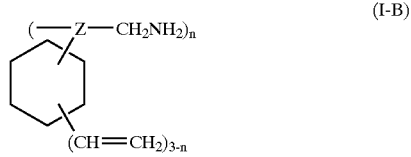

(I-B)

either alone, as mixtures of these, and/or as isomers of these, in which the substituents on the cyclohexane ring are in the 1-, 2-, and 4-positions, Z is a —$CH_2CH_2$— group or a:

group, and n is an integer of 1 to 3.

The inventors have discovered that 1,2,4-trivinylcyclohexane can be contacted with hydrogen cyanide, in the presence of a catalyst and optionally a promoter at a temperature of about −25° C. to about 200° C. and optionally in the presence of a solvent, to yield cyclohexane derivatives of the formula (I-A), wherein the catalyst comprises a Group VIII metal, preferentially nickel, and an organic phosphorous ligand. Further, we have discovered that compounds or mixtures described by (I-A) may be converted to compounds or mixtures described by (I-B) by contacting compounds or mixtures (I-A) with hydrogen, in the presence of a transition metal catalyst at a temperature of 50° C. to 180° C. and a pressure of 50–1500 psig (340 kPa–10340 kPa), optionally in the presence of a solvent. In addition we have discovered that mixture (I-A) can be selectively converted to the mixtures (I-C) and/or (I-D) by a method comprising hydrogenation of the olefin and/or the nitrile group and mixture (I-B) can be selectively converted to mixture (I-D) by hydrogenation of the olefin. These hydrogenations are carried out by contacting (I-A) and/or (I-B) with hydrogen in the presence of one or more transition metal catalysts at a temperature of about 50° C. to about 180° C. and a pressure of about 340 kPa to about 10340 kPa, optionally in the presence of a solvent.

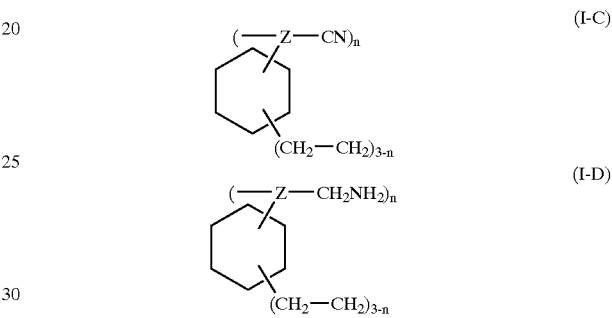

Thus, in one embodiment, the present invention provides a hydrocyanation method for preparing cyclohexane derivatives, having nitrile groups. Generally, the present method yields the present cyclohexane derivatives as a mixture. The method yields several compounds as main products, while other compounds are formed as by-products in varying amounts. The method can be implemented to favor one set of compounds as the main products. The set of compounds favored in this method is a function of process conditions and/or the type of catalyst or catalysts used and/or the type of ligand used and/or the use of an optional promoter. However, it is to be understood that both the individual compounds and also the mixtures thereof are within the scope of the present invention.

The method for making the compounds of the present invention involves a hydrocyanation process with the use of a ligand and a Group VIII metal or compound. Optionally, one may use a Lewis acid in the hydrocyanation process as a promoter, and may optionally use a solvent.

Generally, a Group VIII metal or compound thereof is combined with at least one ligand to provide the catalyst. Among the Group VIII metals or compounds, nickel, cobalt, and palladium compounds are preferred to make the hydrocyanation catalysts. A nickel compound is more preferred. A zero-valent nickel compound that contains a ligand that can be displaced by a ligand of the prior art is the most preferred source of Group VIII metal or Group VIII metal compound.

Zero-valent nickel compounds can be prepared or generated according to methods known in the art. Three preferred zero-valent nickel compounds are $Ni(COD)_2$ (COD is 1,5-cyclooctadiene), $Ni(P(O\text{-}o\text{-}C_6H_4CH_3)_3)_3$ and $Ni\{P(O\text{-}o\text{-}C_6H_4CH_3)_3\}_2(C_2H_4)$; these are known in the art.

Alternatively, divalent nickel compounds can be combined with a reducing agent, to serve as a source of zerovalent nickel in the reaction. Suitable divalent nickel compounds include compounds of the formula $NiX^2_2$ wherein $X^2$ is halide, carboxylate, or acetylacetonate. Suitable reducing agents include metal borohydrides, metal aluminum hydrides, metal alkyls, Li, Na, K, Zn, Al or $H_2$. Elemental nickel, preferably nickel powder, when combined with a halogenated catalyst is also a suitable source of zero-valent nickel.

Suitable ligands for the present invention are monodentate and/or bidentate phosphorous-containing ligands selected from the group consisting of phosphites and phoshinites. Preferred ligands are monodentate and/or bidentate phosphite ligands.

The preferred monodentate and/or bidentate phosphite ligands are of the following structural formulae:

II

III

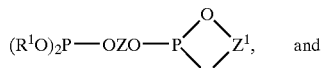 and

IV

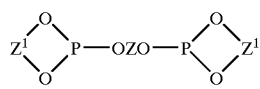

V

In formulae II, III, IV and V, $R^1$ is phenyl, unsubstituted or substituted with one or more $C_1$ to $C_{12}$ alkyl or $C_1$ to $C_{12}$ alkoxy groups; or naphthyl, unsubstituted or substituted with one or more $C_1$ to $C_{12}$ alkyl or $C_1$ to $C_{12}$ alkoxy groups; and Z and $Z^1$ are independently selected from the group consisting of structural formulae VI, VII, VIII, IX, and X:

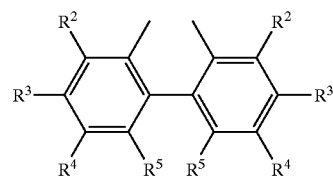

VI

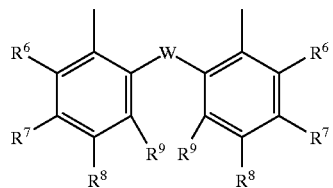

VII wherein:

$R^2$, $R^3$, $R^4$, $R^5$, $R^6$, $R^7$, $R^8$, and $R^9$ are independently selected from H, $C_1$ to $C_{12}$ alkyl, and $C_1$ to $C_{12}$ alkoxy;

W is O, S, or $CH(R^{10})$; $R^{10}$ is H or $C_1$ to $C_{12}$ alkyl;

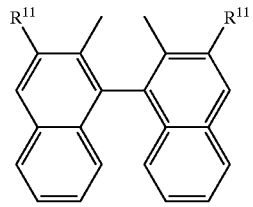

VIII

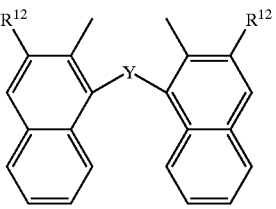

IX wherein:

$R^{11}$ and $R^{12}$ are independently selected from H, $C_1$ to $C_{12}$ alkyl, and $C_1$ to $C_{12}$ alkoxy; and $CO_2R^{13}$, $R^{13}$ is $C_1$ to $C_{12}$ alkyl or $C_6$ to $C_{10}$ aryl, unsubstituted or substituted. with $C_1$ to $C_4$ alkyl Y is O, S, $CH(R^{14})$;

$R^{14}$ is H or $C_1$ to $C_{12}$ alkyl:

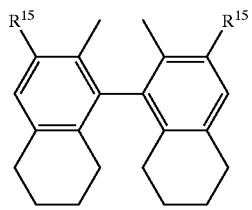

X wherein $R^{15}$ is selected from H, $C_1$ to $C_{12}$ alkyl, and $C_1$ to $C_{12}$ alkoxy; and $CO_2R^{16}$, $R^{16}$ is $C_1$ to $C_{12}$ alkyl or $C_6$ to $C_{10}$ aryl, unsubstituted or substituted with $C_1$ to $C_4$ alkyl In the structural formulae II through X, the $C_1$ to $C_{12}$ alkyl, and $C_1$ to $C_{12}$ alkoxy groups may be straight chains or branched.

Examples of bidentate phosphite ligands that are useful in the present process include those having the formulae XI to XXXIV, shown below wherein for each formula, $R^{17}$ is selected from the group consisting of H, methyl, ethyl or isopropyl, and $R^{18}$ and $R^{19}$ are independently selected from H or methyl:

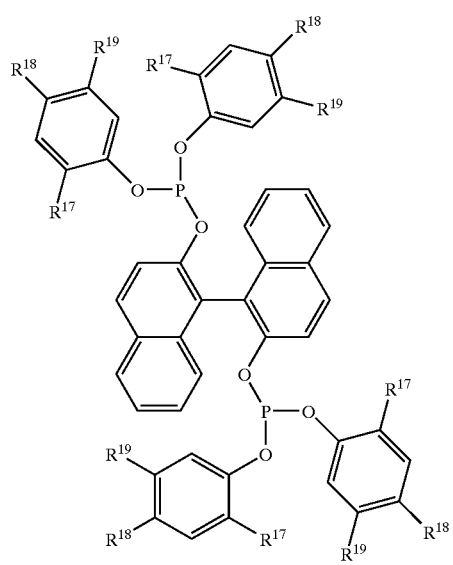
XI
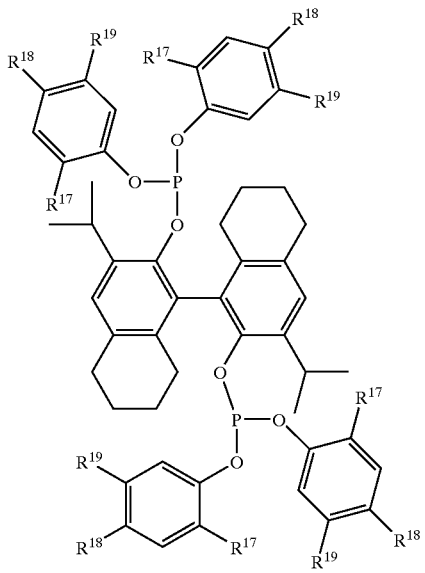
XIII
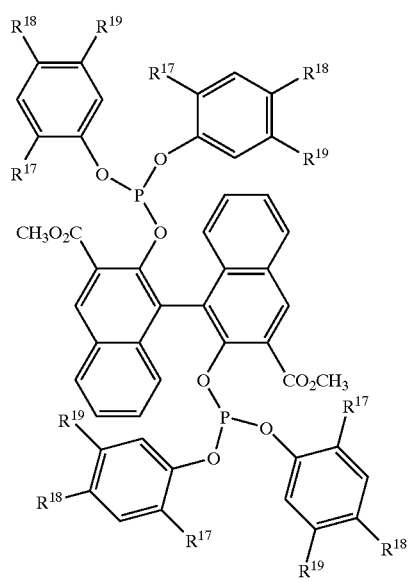
XII
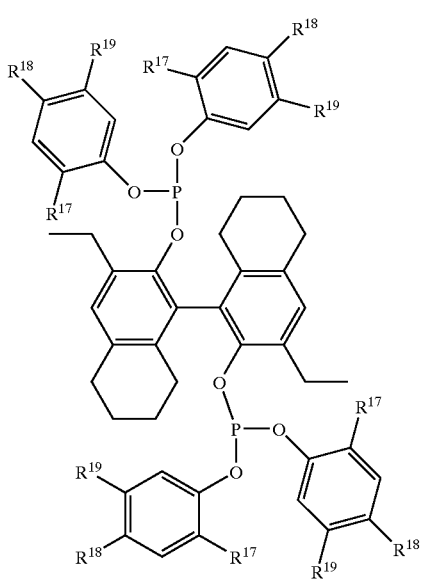
XIV

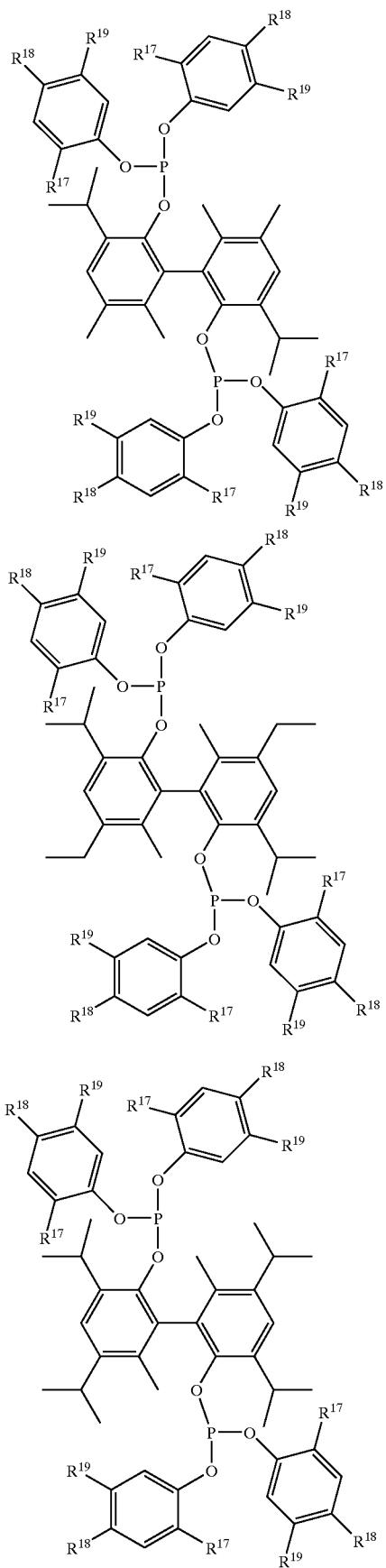
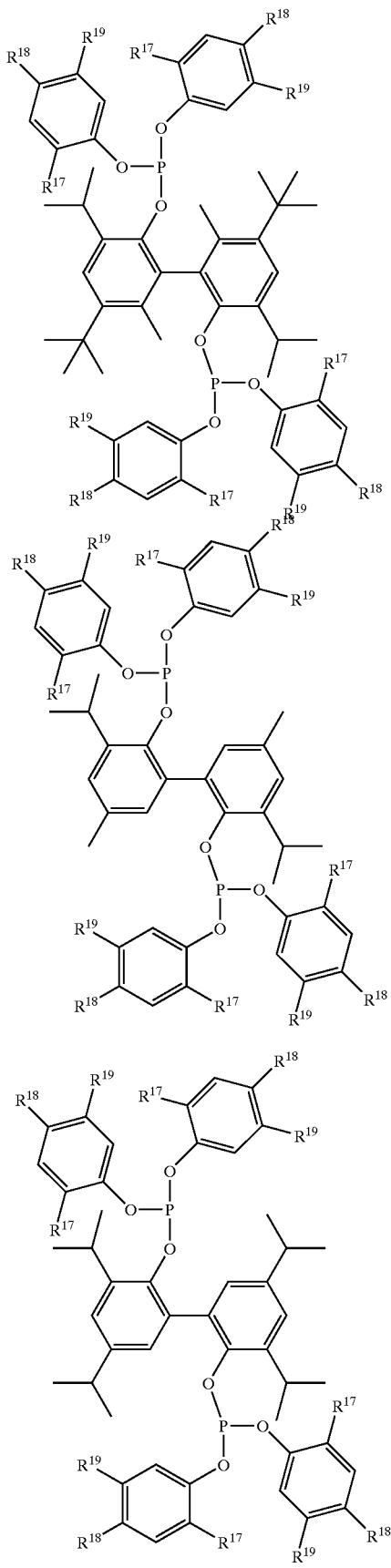

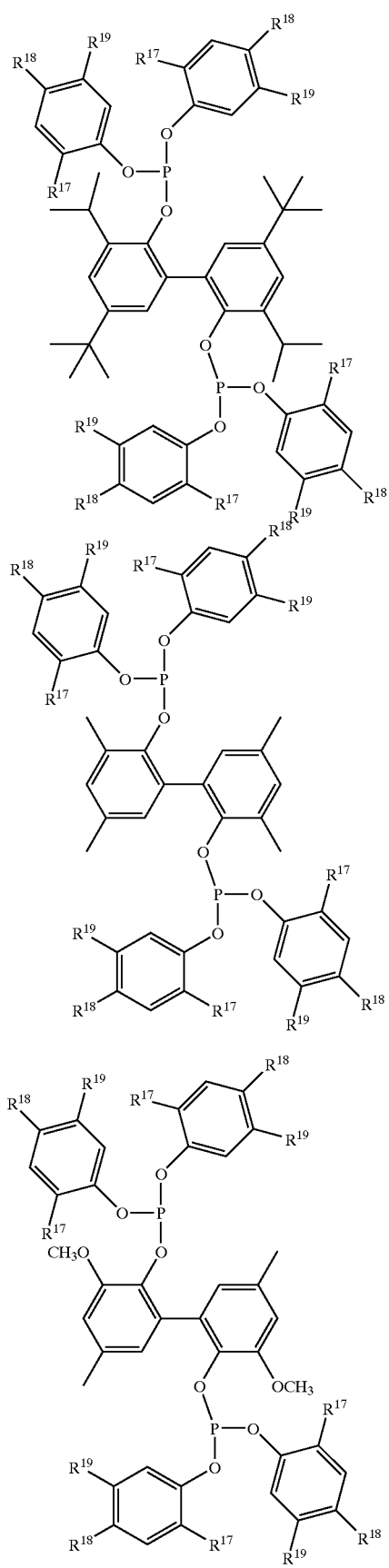

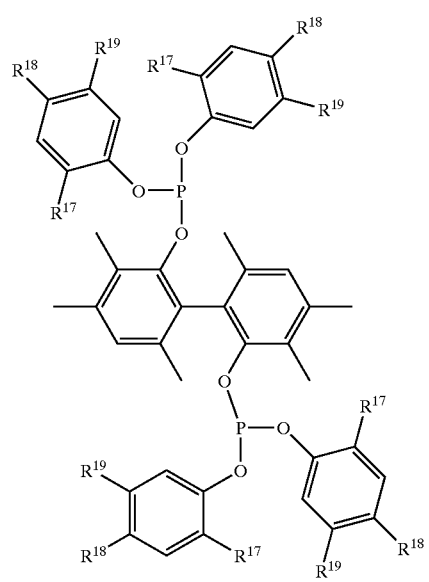
XXVII
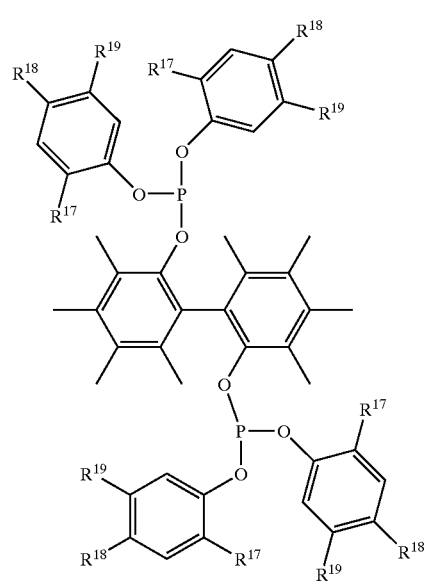
XXVIII
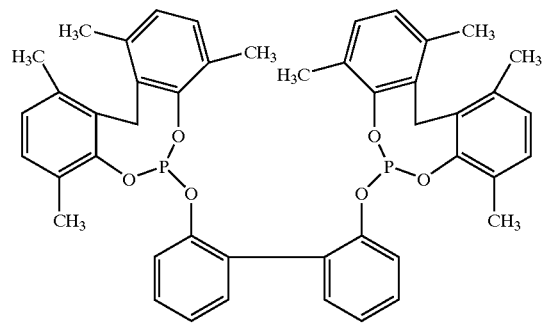
XXIX
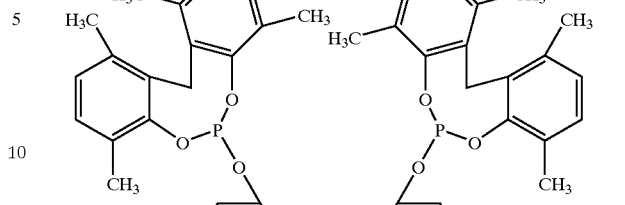
XXX
XXXI
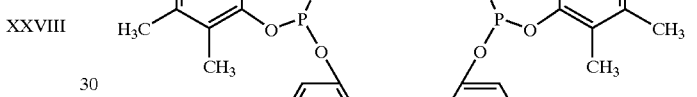
XXXIII
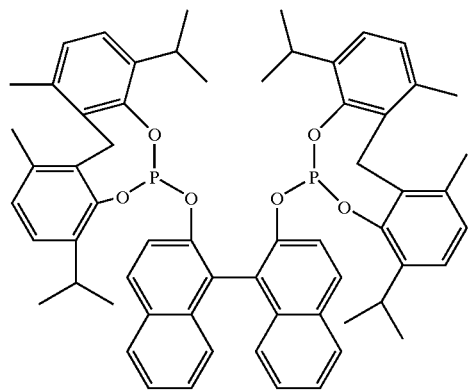
XXXIV

XXXV

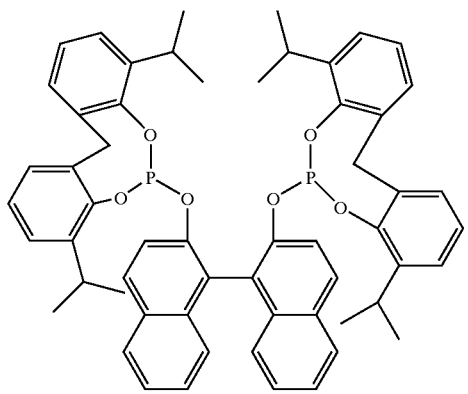

Suitable bidentate phosphites are of the type disclosed in U.S. Pat. Nos. 5,512,695; 5,512,696; 5,663,369; 5688,986; 5,723,641; 5,847,191; 5,959,135; 6,120,700; 6,171,996; 6,171,997; 6,399,534; the disclosures of which are incorporated herein by reference. Suitable bidentate phosphinites are of the type disclosed in U.S. Pat. Nos. 5,523,453 and 5,693,843, the disclosures of which are incorporated herein by reference.

A preferred embodiment of this invention is the use of a bidentate phosphite ligand of the formula XVIII, XIII, XXI, or XXVI in combination with the Group VIII metal, preferably nickel, as catalyst for the hydrocyanation process.

The ratio of ligand to active nickel can vary from a ligand to nickel ratio of 0.5:1 to a ligand to nickel ratio of 100:1. Preferentially the ligand to nickel ratio ranges from 1:1 to 4:1. The ligands of the present invention contain trivalent phosphorus atoms in which each trivalent phosphorous atom is known as phosphite. The ligands useful in the present invention can be mono-dentate ligands and/or bidentate ligands meaning that two trivalent phosphorus atoms in the molecule are each bonded to the same organic group, which bridges the trivalent phosphorus atoms together. The ligands in the present invention can also be multidentate with a number of phosphorous atoms in excess of 2 or of polymeric nature in which the ligand/catalyst composition is not homogeneously dissolved in the process mixture.

Optionally, the process of this invention is carried out in the presence of one or more Lewis acid promoters that affect both the activity and the selectivity of the catalyst system. The promoter may be an inorganic or organometallic compound in which the cation is selected from scandium, titanium, vanadium, chromium, manganese, iron, cobalt, copper, zinc, boron, aluminum, yttrium, zirconium, niobium, molybdenum, cadmium, rhenium and tin. Examples include but are not limited to $ZnBr_2$, $ZnI_2$, $ZnCl_2$, $ZnSO_4$, $CuCl_2$, $CuCl$, $Cu(O_3SCF_3)_2$, $CoCl_2$, $CoI_2$, $FeI_2$, $FeCl_3$, $FeCl_2$, $FeCl_2(THF)_2$, $TiCl_4(THF)_2$, $TiCl_3$, $TiCl_2$, $ClTi(OiPr)_2$, $MnCl_2$, $ScCl_3$, $AlCl_3$, $(C_8H_{17})AlCl_2$, $(C_8H_{17})_2AlCl$, $(iso-C_4H_9)_2AlCl$, $(C_6H_5)_2AlCl$, $(C_6H_5)AlCl_2$, $ReCl_5$, $ZrCl_4$, $NbCl_5$, $VCl_3$, $CrCl_2$, $MoCl_5$, $YCl_3$, $CdCl_2$, $LaCl_3$, $Er(O_3SCF_3)_3$, $Yb(O_2CCF_3)_3$, $SmCl_3$, $B(C_6H_5)_3$, $R^{20}SnO_3SCF_3$ where $R^{20}$ is an alkyl or aryl group). Preferred promoters include $CdCl_2$, $FeCl_2$, $ZnCl_2$, $CoCl_2$, $COI_2$, $AlCl_3$, $B(C_6H_5)_3$, and $(C_6H_5)_3Sn(CF_3SO_3)$. The mole ratio of promoter to Group VIII transition metal present in the reaction can be within the range of about 1:16 to about 50:1, with 0.5:1 to about 2:1 being preferred.

The ligand compositions of the present invention may be used to form catalysts, which may be used for the hydrocyanation of 1,2,4-trivinylcyclohexane, with or without a Lewis acid promoter.

The process comprises contacting, in the presence of the catalyst, 1,2,4-trivinylcyclohexane with a hydrogen cyanide-containing fluid under conditions sufficient to produce a nitrile. Any fluid containing about 1 to 100% HCN can be used. Pure hydrogen cyanide may be used.

The hydrocyanation process can be carried out, for example, by charging a suitable vessel, such as a reactor, with 1,2,4-trivinylcyclohexane, catalyst and optionally solvent, to form a reaction mixture. Hydrogen cyanide can be initially combined with other components to form the mixture. However, it is preferred that HCN be added slowly to the mixture after other components have been combined. Hydrogen cyanide can be delivered as a liquid or as a vapor to the reaction. As an alternative, a cyanohydrin can be used as the source of HCN as known in the art.

Another suitable technique is to charge the vessel with the catalyst and the solvent (if any) to be used, and feed both the 1,2,4-trivinylcyclohexane and the HCN slowly to the reaction mixture.

The molar ratio of 1,2,4-trivinlycyclohexane to catalyst can be varied from about 10:1 to about 10,000:1. The molar ratio of HCN: catalyst can be varied from 5:1 to 10,000:1. The process can be run in continuous or batch mode.

Preferably, the reaction mixture is agitated, for example, by stirring or shaking. The present compounds can be individually isolated from the reaction mixture, using known conventional methods, such as chromatography or fractional distillation.

The hydrocyanation can be carried out with or without a solvent. The solvent, if used, can be liquid at the reaction temperature and pressure and inert towards 1,2,4-trivinylcyclohexane and the catalyst. Examples of suitable solvents include hydrocarbons such as benzene, xylene, or combinations thereof; ethers such as tetrahydrofuran (THF), nitriles such as acetonitrile, adiponitrile, or combinations of two or more thereof. 1,2,4-trivinylcyclohexane can itself serve as the solvent.

The exact temperature is dependent to a certain extent on the particular catalyst being used, and the desired reaction rate. Normally, temperatures of from −25° C. to 200° C. can be used, the range of about 0° C. to about 120° C. being preferred.

The process can be run at atmospheric pressure. Pressures of from about 50.6 to 1013 kPa are preferred. Higher pressures, up to 10,000 kPa or more, can be used, if desired.

The time required can be in the range of from a few seconds to many hours (such as 2 seconds to 72 hours), depending on the particular conditions and method of operation.

In a first preferred embodiment, the present invention relates to compounds with the general structure of formula (XXXVI):

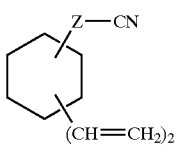
(XXXVI)

alone or in mixtures with one another, their production, and derivatives prepared from such compounds. For the production of the compounds of formula XXXVI, 1,2,4-trivinylcyclohexane is reacted with hydrogen cyanide in the presence of a group VIII catalyst, preferably nickel, a ligand and optionally a Lewis acid promoter. In this embodiment, a product mixture is obtained which generally comprises cyclohexane derivatives having linear nitrites and two olefinic groups. For example, the product obtained comprises a mixture of formulae XXXVII, XXXVIII and XXXIX. Isomers, represented by formula XL, XLI and XLII may be present in small amounts.

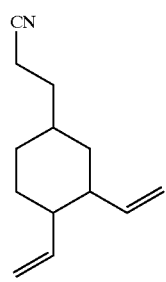
(XXXVII)

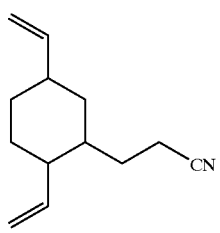
(XXXVIII)

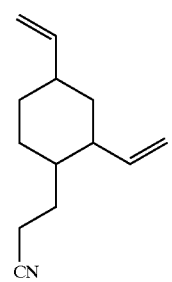
(XXXIX)

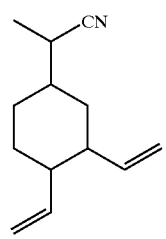
(XL)

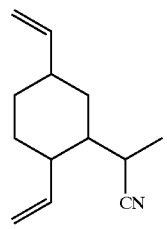
(XLI)

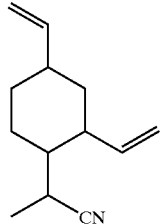
(XLII)

In another preferred embodiment, the present invention relates to compounds with the general structure of formula (XLIII):

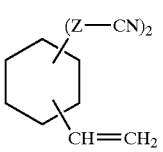
(XLIII)

alone or in a mixture with one another, their production, and derivatives prepared from such compounds. For the production of the compounds of formula XLIII, 1,2,4-trivinylcyclohexane is reacted with hydrogen cyanide in the presence of a Group VIII catalyst, preferably nickel, a ligand and, optionally, a Lewis acid promoter. In this embodiment, a product is obtained that comprises a mixture of formulae XLIV, XLV and XLVI:

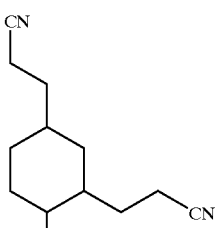
(XLIV)

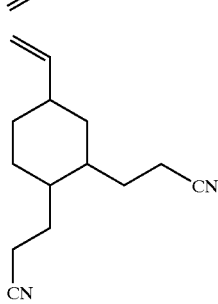
(XLV)

(XLVI)
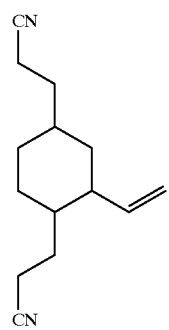
(XLVII)
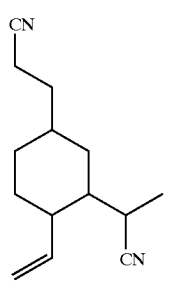
(XLVIII)
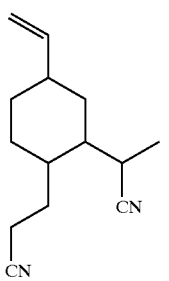
(XLIX)
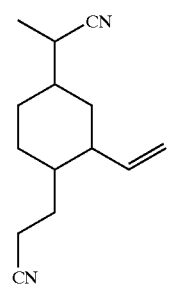
(L)
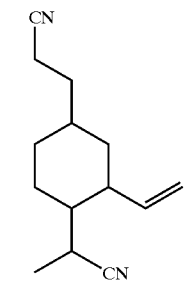
(LI)
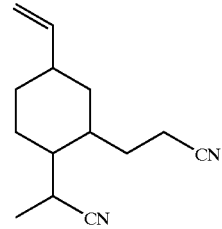
(LII)
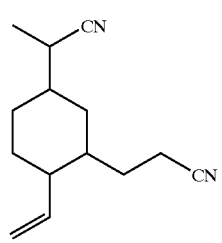
(LIII)
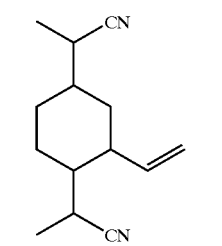
(LIV)
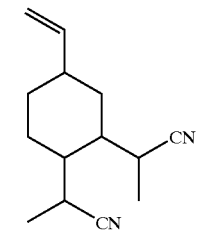
(LV)
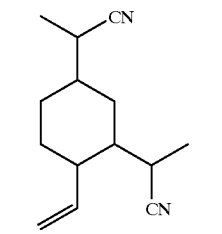
Isomers, represented by formulae XLVII through LV may be present in smaller amounts.
In a third preferred embodiment, the invention relates to compounds with the general structure of formula (LVI):
(LVI)
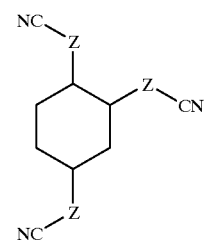

alone or in a mixture with one another, their production, and derivatives prepared from such compounds wherein Z is defined as above. For the production of the compounds of formula LVI, 1,2,4-trivinylcyclohexane is reacted with hydrogen cyanide in the presence of a group VIII catalyst, preferentially nickel, a ligand and, optionally a Lewis acid promoter. In this embodiment, a product mixture is obtained that comprises LVII and to a smaller extent compounds LVIII through LXIV:

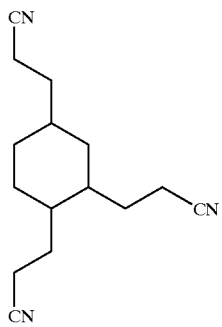
(LVII)

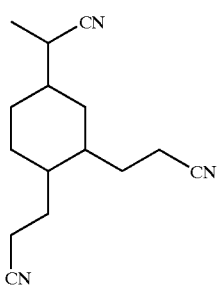
(LVIII)

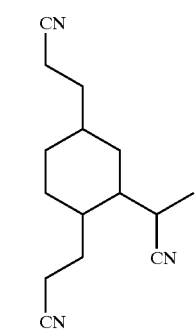
(LIX)

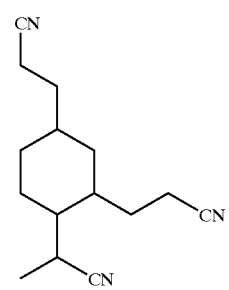
(LX)

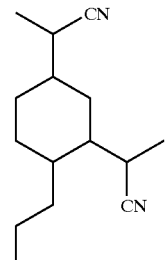
(LXI)

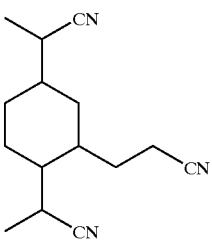
(LXII)

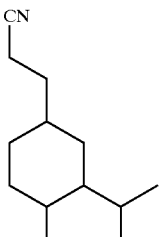
(LXIII)

(LXIV)

The present cyclohexane derivatives containing nitrile groups can be used alone or in mixtures with one another, for further functionalization. For example, they can be converted to their corresponding amines by hydrogenation. Thus compounds described by (I-A) either alone or as mixtures of isomers may be contacted with hydrogen in the presence of a catalyst, optionally in the presence of a solvent to yield amine compounds described by (I-B).

During the hydrogenation process the feed (i.e. compounds described by (I-A) either alone or in mixtures of isomers) is contacted with hydrogen. The mole ratio of hydrogen to feed is not critical as long as sufficient hydrogen is present to produce the desired derivatives described by (I-B). Hydrogen is preferably used in excess. Hydrogen pressures are generally in the range of about 340 kPa–10340 kPa, with about 1480 to about 7000 kPa preferred. The hydrogenation process can be conducted at temperatures from 50° C. to about 180° C., preferably from 65° C. to about 100° C.

Preferred catalysts for hydrogenating nitriles to amines comprise one or more elements from the series of transition metals, particularly useful are iron, cobalt, nickel, rhodium and combinations thereof. The hydrogenation catalyst may also comprise one or more elements in addition to the transition metals mentioned above, for example, elements of Group IA (including lithium, sodium and potassium), elements of Group IIA (including magnesium and calcium), titanium, elements of Group VI (including chromium, molybdenum and tungsten), elements of Group VIII (including palladium) and/or aluminum, silicon, boron and/or phosphorous. The hydrogenation catalyst can also be in the form of an alloy, including a solid solution of two or more elements.

The transition metal for hydrogenation can also be supported on an inorganic support such as alumina, magnesium oxide and combinations thereof. The metal can be supported on an inorganic support by any means known to one skilled in the art such as, for example, impregnation, co-precipitation, ion exchange, or combinations of two or more thereof. The metal can be reduced before the hydrogenation reaction by any means known to one skilled in the art such as, for example, pretreatment with hydrogen, formaldehyde or hydrazine.

The hydrogenation catalyst can be present in any appropriate physical shape or form. It can be in fluidizable forms, powders, extrudates, tablets, spheres or combinations of two or more thereof. The hydrogenation catalyst may be in sponge metal form, for example, the Raney® nickels and Raney® cobalts. The molar ratio of hydrogenation catalyst to feed (i.e. compounds described by (I-A) either alone or in mixtures and/or isomers) can be any ratio as long as the ratio can catalyze the hydrogenation. The weight ratio of hydrogenation catalyst to feed is generally in the range of from about 0.0001:1 to about 1:1, preferably about 0.001:1 to about 0.5:1. If the catalytic element is supported on an inorganic support or is a portion of an alloy or solid solution, the catalytic element is generally present in the range of from about 0.1 to about 60, preferably about 1 to about 50, and most preferably about 2 to about 50 weight percent based on the total hydrogenation catalyst weight.

The preferred nitrile hydrogenation catalyst is a sponge metal type catalyst. The metallic component is iron, cobalt, nickel or combinations thereof. Commercially available catalysts of this type are promoted or un-promoted Raney® Ni or Raney® Co catalysts that can be obtained from the W.R. Grace and Co. (Chattanooga, Tenn.), or alternative sponge metal catalysts available, for example, from Activated Metals Corporation (Sevierville, Tenn.) or Degussa (Parsippany, N.J.).

The hydrogenation can optionally be conducted in the presence of a solvent. Suitable solvents include those known in the art as useful for hydrogenation reactions. Examples of these are amines, aliphatic alcohols, aromatic compounds, ethers, esters (including lactones), and amides (including lactams). Specific examples of solvents include: ammonia, toluene, tetrahydrofuran, methanol, ethanol, any isomeric propanol, any isomeric butanol and water. Preferred solvents include ammonia, toluene and methanol. It will be appreciated that the solvent may serve to reduce the viscosity of the system to improve fluidity of the catalyst in the reaction vessel, as well as serve to remove the heat of reaction from the feed and products. The solvent may be present in a range of 1% to 75% by weight of the total reaction mixture, excluding the catalyst, preferably from 10% to 50%.

Optionally, a promoter may be used in the hydrogenation process to alter the rate of the reaction and/or alter the selectivity of the reaction. Suitable promoters include water, alkali or alkaline earth metal hydroxides, quaternary ammonium hydroxides, quaternary ammonium cyanides, quaternary ammonium fluorides, and combinations of these. Promoters may be present at from 10 ppm to 3% by weight of the total reaction mixture, excluding the catalyst, preferably from 50 ppm to 1.5%.

It will be further appreciated that any olefin content of products described by (I-A) or (I-B) (i.e. any carbon-carbon double bonds) may be saturated using the instant hydrogenation with the further specification that the preferred catalyst for hydrogenation of the olefin comprises palladium, rhodium, nickel and/or ruthenium. Hydrogenation of the olefin content can occur before, during or after the hydrogenation of the nitrile content to amine. This process produces compounds (I-C) and/or compounds (I-D). The products according to the present invention can be used as monomers for the production of polymers, or as fragrance intermediates.

Having generally described this invention, a further understanding can be obtained by reference to certain specific examples, which are provided herein for purpose of illustration only and are not intended to be limiting unless otherwise specified.

EXAMPLES

Examples 1–8—Hydrocyanation

A solution of catalyst was prepared by combining $Ni(COD)_2$ in toluene with the phosphite ligand in a ratio of Ni:ligand of 1:1.1. This solution was sampled into a reaction vessel. 1,2,4-trivinylcyclohexane was added to the reaction vessel, the ratio of 1,2,4-trivinylcyclohexane to catalyst was 70:1. A solution of promoter was prepared by adding $ZnCl_2$ to acetonitrile with a ratio of Ni to Zn of 1:1. This solution was added to the reaction vessel. Hydrogen cyanide was added to the reaction vessel via vapor feed. The hydrogen cyanide reservoir was at room temperature while the reaction vessel was maintained at 50° C. The reaction was carried out for 24 hours after which time the samples were analyzed by standard GC methodology for products. All products were analyzed by MS and NMR spectroscopy and compared to analytical data obtained for isolated fractions.

| Entry | Ligand | Promoter | Conversion [%] | Compound [%] | | |
|---|---|---|---|---|---|---|
| | | | | (XXXVI) | (XLIII) | (LVI) |
| 1 | 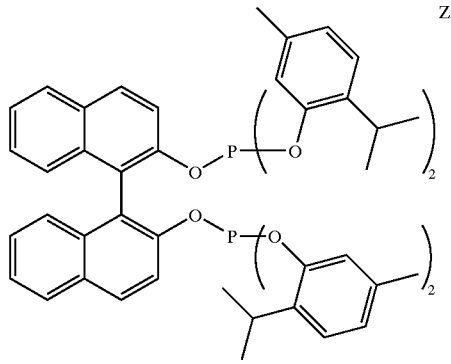 | ZnCl$_2$ | 99.7 | 1.3 | 15.5 | 82.8 |
| 2 | 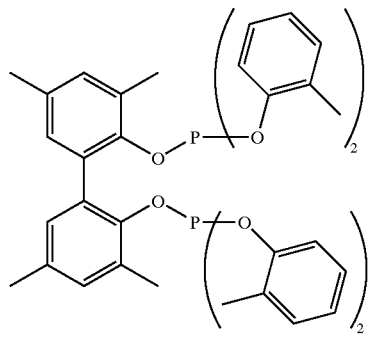 | ZnCl$_2$ | 99.3 | 8.6 | 39.0 | 51.7 |
| 3 | 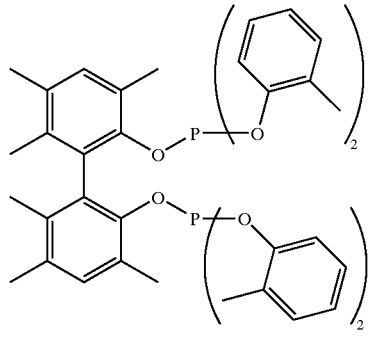 | ZnCl$_2$ | 84.7 | 41.8 | 33.1 | 9.9 |
| 4 | 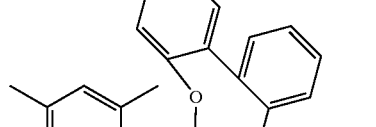 | none | 88.7 | 62.0 | 25.2 | 1.5 |
| 5 | 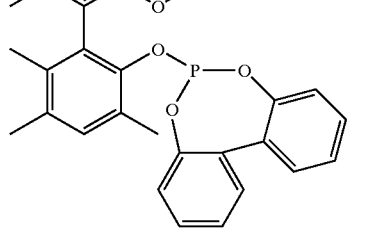 | ZnCl$_2$ | 87.1 | 44.2 | 34.2 | 8.7 |

| Entry | Ligand | Promoter | Conversion [%] | Compound [%] (XXXVI) | (XLIII) | (LVI) |
|---|---|---|---|---|---|---|
| 6 | | ZnCl₂ | 87.4 | 41.7 | 35.3 | 10.4 |
| 7 | | ZnCl₂ | 76.6 | 47.9 | 24.9 | 3.8 |
| 8 | | ZnCl₂ | 84.5 | 45.4 | 30.6 | 8.5 |
Example 9—Hydrocyanation
In a 500 ml flask 1,2,4-trivinylcyclohexane (100 g, 0.62 mol) was mixed with a toluene (10 g) solution of Ni(COD)₂ (0.85 g, 3.1 mmol) and the following ligand (2.58 g, 3.4 mmol), XXVI with R17=Me, R18, R19=H.
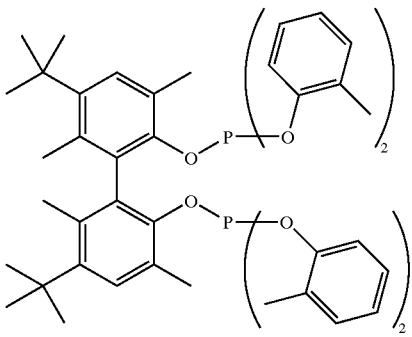

To this was added a solution of ZnCl$_2$ (0.46 g, 3.4 mmol) in acetonitrile (10 ml). A solution of hydrogen cyanide (52 g, 1.91 mol) in acetonitrile (77.6 g) was prepared and added to the above mixture using a syringe pump. During 1 hour and 45 minutes a feed rate of 115.6 ml/hour was maintained at 50° C. Product composition was analyzed as follows:

|  | (XXXVI) | (XLIII) | (LVI) |
| --- | --- | --- | --- |
| 60 minutes | 13.15% | 43.2% | 40.4% |
| 120 minutes | 0.95% | 12.66 | 85.23% |

Example 10—Hydrocyanation

In a flask 1,2,4-trivinylcyclohexane (50 g, 0.31 mol) was mixed with a toluene (25 g) solution of Ni(COD)$_2$ (0.42 g, 1.6 mmol) and the following ligand (R$^1$O)$_3$P, II, (4.78 g, 15.4 mmol) with R$^1$=—C$_6$H$_5$. To this was added a solution of ZnCl$_2$ (0.21 g, 1.5 mmol) in acetonitrile (10 ml). A solution of hydrogen cyanide (8.3 g, 0.31 mol) in acetonitrile (12.5 g) was prepared and added to the above mixture using a syringe pump. After 17 hours at 50C with a feed rate of 1.5 ml/hour the product composition was analyzed as follows:

|  | (XXXVI) | (XLIII) | (LVI) |
| --- | --- | --- | --- |
| 17 hours | 15.0% | 0.8% | — |

Example 11—Hydrogenation

To a 100 cc stirred pressure reactor were added 21.18 g of (LVI), 4 g methanol, and 2 g Raney® Co 2724 slurry (Grace Davison Catalysts, Chattanooga, Tenn.). The reactor was sealed, checked for leaks and then charged with 30 g anhydrous ammonia. The reactor was pressurized to 250 psig with hydrogen and heated to 75° C. at which point the pressure was increased to 900 psig with hydrogen. The reaction proceeded 12 hours, during which time hydrogen was replenished to the reactor as needed to maintain a pressure of 900 psig in the reactor. Upon completion of the reaction the mixture was filtered and distilled under vacuum to yield 18.45 g of a colorless product. The product exhibited infrared and nuclear magnetic resonance spectra consistent with the absence of nitrile and the presence of amine.

Example 12—Hydrogenation

To a 100 cc stirred pressure reactor were added 22.3 g of (XLIII), 2.0 g methanol, and 2 g Raney® Co 2724 slurry. The reactor was sealed, checked for leaks and then charged with 30 g anhydrous ammonia. The reactor was pressurized to 250 psig with hydrogen and heated to 75° C. at which point the pressure was increased to 900 psig with hydrogen. The reaction proceeded 6 hours, during which time hydro gen was replenished to the reactor as needed to maintain a pressure of 900 psig in the reactor. Upon completion of the reaction the mixture was filtered and the solvent removed by evaporation. The product exhibited infrared (IR) and nuclear magnetic resonance (NMR) spectra consistent with the absence of nitrile and the presence of amine and olefin, i.e. olefin remained in the molecule and available for further functionalization or hydrogenation. The product was next added to a 100 cc stirred pressure reactor along with 2 g of 5% Pd/carbon catalyst, and 30 g of tetrahydrofuran and heated at 75° C. with hydrogen at 500 psig pressure for 4 hours. Since the product NMR suggested that olefin content still remained in the product it was submitted to additional hydrogenation with 5% Pd/carbon catalyst. The final product mixture was filtered and distilled under vacuum to yield 14.51 g of a colorless product with NMR and IR spectra consistent with the absence of nitrile and olefin but the presence of amine.

What is claimed:

1. A compound of formula (I-A):

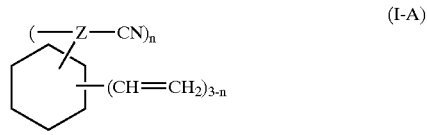

wherein substituents on the cyclohexane ring are in the 1-, 2-, and 4-positions, and wherein Z is a —CH$_2$CH$_2$— group or a

group, and n is an integer of 1 to 3.

2. A method for preparing the compound of claim 1 comprising:

contacting 1,2,4-trivinylcyclohexane with hydrogen cyanide, in the presence of a catalyst, said catalyst comprising an organic phosphorous ligand and a Group VIII metal, wherein said contacting is done at a temperature of from about −25° C. to about 200° C.

3. The method of claim 2 wherein said contacting is done in the presence of a Lewis acid promoter.

4. The method of claim 2 or 3 wherein said contacting is done in the presence of a solvent.

5. The compound of claim 1 consisting of formula XXXVL:

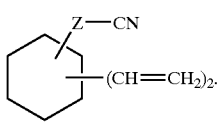

6. The compound of claim 5 consisting of any of the formulae XXXVII to XLII:
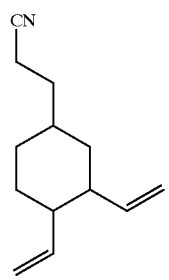
(XXXVII)
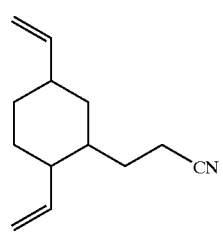
(XXXVIII)
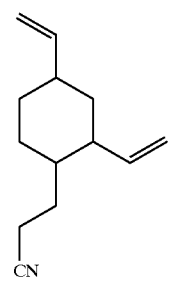
(XXXIX)
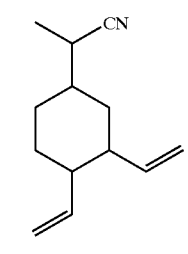
(XL)
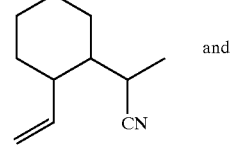
and
(XLI)
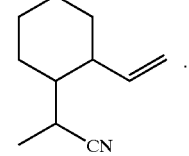
(XLII)
7. A composition, comprising two or more compounds of any two or more of formulae XXXVII to XLII of claim 6.
8. The compound of claim 1 consisting of formula XLIII:
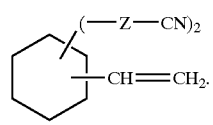
XLIII
9. The compound of claim 8 consisting of any of the formulae XLIV to LV:
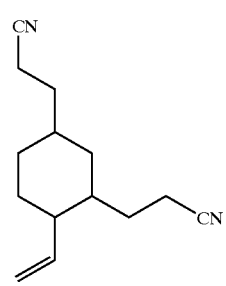
(XLIV)
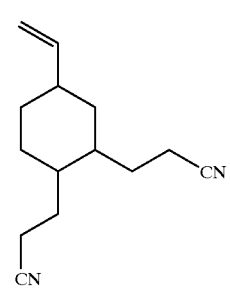
(XLV)
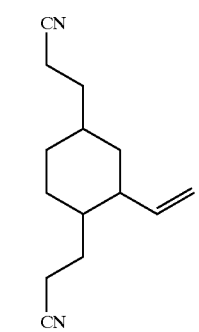
(XLVI)
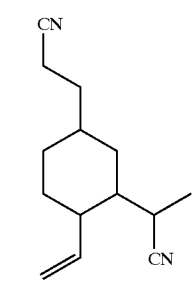
(XLVII)

(XLVIII)
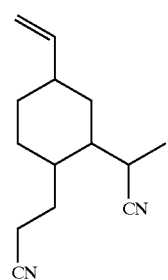
(XLIX)
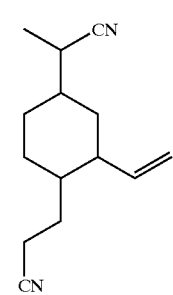
(L)
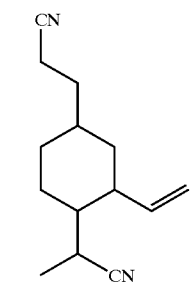
(LI)
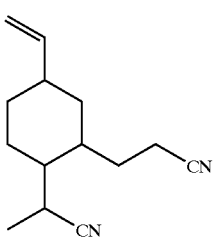
(LII)
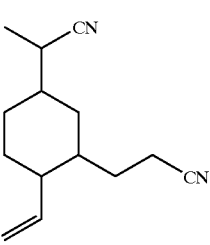
(LIII)
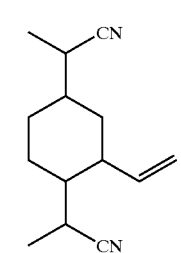
(LIV)
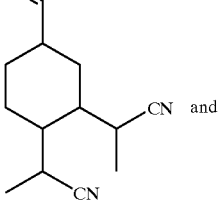 and
(LV)
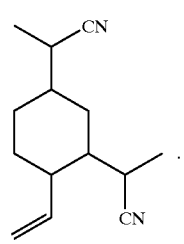
10. A composition comprising two or more compounds of any two or more of formulae XLIV to LV of claim 9.
11. The compound of claim 1 consisting of formula LVI:
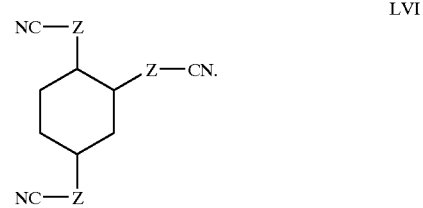
LVI
12. The compound of claim 11 consisting of any of the formulae LVII to LXIV:
(LVII)
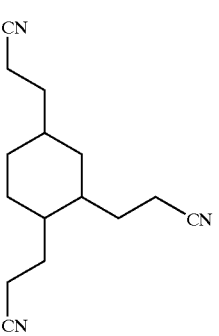
(LVIII)
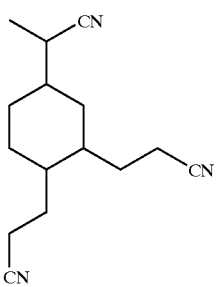

-continued
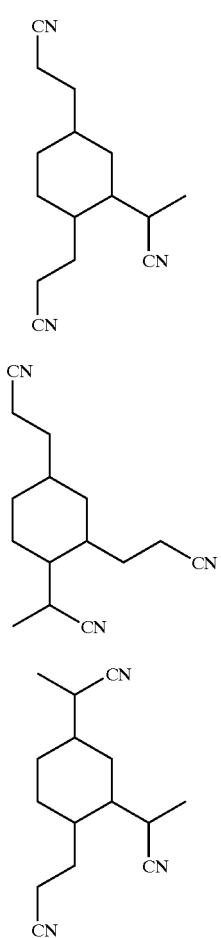
(LIX)
(LX)
(LXI)
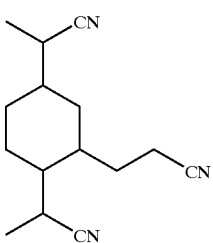
(LXII)
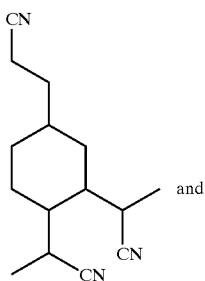
(LXIII)
and
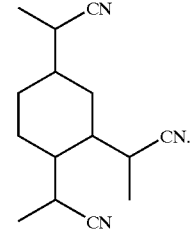
(LXIV)
13. A composition comprising two or more compounds of any two or more of formulae LVII to LXIV of claim 12.
14. A composition comprising two or more compounds of formula I-A of claim 1.
* * * * *